United States Patent [19]

Buser et al.

[11] Patent Number: 5,792,795
[45] Date of Patent: Aug. 11, 1998

[54] TREATMENT OF INFLAMMATORY BOWEL DISEASE USING ORAL DOSAGE FORMS OF OMEGA-3 POLYUNSATURATED ACIDS

[75] Inventors: Thomas Buser, Ziefen; Emilio P. Camporesi, Ziefen, both of Switzerland

[73] Assignee: Tillotts Pharma AG, Ziefen, Switzerland

[21] Appl. No.: 687,329

[22] PCT Filed: May 13, 1996

[86] PCT No.: PCT/EP96/02038

§ 371 Date: Aug. 7, 1996

§ 102(e) Date: Aug. 7, 1996

[87] PCT Pub. No.: WO96/36329

PCT Pub. Date: Nov. 21, 1996

[30] Foreign Application Priority Data

May 15, 1995 [GB] United Kingdom ............... 9509764

[51] Int. Cl.$^6$ .................................................. A61K 31/20
[52] U.S. Cl. .................................... 514/560; 514/963
[58] Field of Search ............................. 514/560, 963

[56] References Cited

U.S. PATENT DOCUMENTS 5,252,333  10/1993  Horrobin ........................ 424/422
5,411,988   5/1995  Bockow et al. .................. 514/560
5,422,115   6/1995  Horrobin ........................ 424/422
5,603,953   2/1997  Herbig et al. ................... 424/473

FOREIGN PATENT DOCUMENTS 225303   6/1987  European Pat. Off. .
289204  11/1988  European Pat. Off. .
2223943  4/1990  United Kingdom .

OTHER PUBLICATIONS

Rohm Pharma Gmbh brochure titled "Sustained-release coatings with Eudragit® NE 30D from aqueous dispersions" (1995).

Belluzzi, A., et al, abstract titled "New Fish Oil Derivative for Preventing Clinical Relapses in Crohn's Disease: A Double Blind Placebo Controlled Randomized Trail", published Digestive Disease Weekly 14 May 1995.

*Primary Examiner*—Kimberly Jordan

[57] ABSTRACT

Inflammatory bowel disease, especially Crohn's disease and ulcerative colitis, is treated by administration of an oral dosage form, containing as an active principle an omega-3 polyunsaturated acid in free acid form or as a pharmaceutically acceptable salt thereof, which releases the acid in the ileum. Preferably the oral dosage form is a gelatine capsule coated with a poly(ethylacrylate-methylmethacrylate).

17 Claims, No Drawings

TREATMENT OF INFLAMMATORY BOWEL DISEASE USING ORAL DOSAGE FORMS OF OMEGA-3 POLYUNSATURATED ACIDS

This application is a 371 of PCT/EP96/02038, filed May 13, 1996.

The present invention relates to the oral administration of omega-3 polyunsaturated acids especially, but not exclusively, eicosapenta-5,8,11,14,17-enoic acid ("EPA") and/or docosahexa-4,7,10,13,16,19-enioc acid ("DHA"). In particular, it provides enteric dosage forms of omega-3 polyunsaturated acids for the treatment of inflammatory bowel disease especially, but not exclusively, Crohn's disease and ulcerative colitis.

It is known that DHA, EPA and other omega-3 polyunsaturated acids are of use in the treatment of inflammatory bowel disease (see, for example, EP-A-0244832, EP-A-0289204, EP-A-0311091 & WO-A-93/21912).

EP-A-0244832 discloses pharmaceutical compositions containing certain unsaturated fatty acids with certain specified stimulators. The compositions are of use for treating disorders associated with prostaglandin deficiency, especially gastrointestinal ulcers. The unsaturated fatty acids are those which have 3 to 5 isolated double bonds and 18 to 22 carbon atoms arranged in a straight chain and are capable of being methylated or ethylated at one or two carbon atoms in positions 2, 3, 4, 16, 17, 18, 19 or 20. EPA is amongst the exemplified acids. Reference is made to pH dependent delayed release formulations containing polystyrene or polyacrylic derivatives and to enteric coated products.

EP-A-0289204 discloses disinfectant and pharmaceutical compositions comprising the lithium salt of a $C_{18}$–$C_{22}$ polyunsaturated fatty acid. Specified polyunsaturated fatty acids include DHA and EPA. The pharmaceutical compositions can be for enteral, parenteral and topical administration and are for use in the treatment of conditions responsive to lithium and/or polyunsaturated fatty acid therapy. Specified conditions responsive to polyunsaturated fatty acid therapy include Crohn's disease and ulcerative colitis. Reference is made to providing an enteric coat of, for example, an acrylate or cellulose acetate phthalate to delay release of the salt until the intestine.

EP-A-0311091 discloses physiologically acceptable isotonic fat emulsions containing an omega-3-fatty acid or ester, a medium-chain length triglyceride, and an emulsifier. The fatty acid or ester component can be present as a pure compound or in the form of a fish oil and preferably is EPA. The emulsion is administered parenterally for, inter alia, treatment of chronic inflammatory bowel disease.

WO-A-93/21912 discloses the use of emulsions containing a polyunsaturated long-chain omega-3-fatty acid or ester for parenterally administration to treat inflammatory disorders including inflammatory bowel disease. The fatty acid or ester can be present as fish oil and preferred fatty acids include DHA and EPA.

Enteric coated products containing DHA or EPA have been reported for use in the treatment of other conditions (see EP-A-0336662, GB-A-2090529, JP-A-62201823, & WO-A-90/04391)

EP-A-0336662 discloses the micro encapsulation of fish oil acids within an enteric coating to provide a stable, odorless and tasteless composition for incorporation into a food product to reduce plasma triglyceride, low density lipoprotein and cholesterol levels. The specified coating materials are ethyl cellulose, cellulose acetate phthalate and cellulose acetate trimelitate. Reference is made to release of the active below the pylorus in the upper portion of the intestine but there is no specific reference to targeting release to the ileum.

GB-A-2090529 discloses the prophylaxis and treatment of thrombosis using DHA or esters or amides thereof. Reference is made in general terms to intestine soluble coated tablets and to film coated tablets.

JP-A-62201823 discloses enterically coated capsules for treating enteral abnormal fermentation or diarrhoea which contain bacteria in an oil. The oil can be EPA and a number of enteric materials are specified including shellac, carboxymethyl cellulose, cellulose acetate phthalate, hydroxymethyl propylcellulose phthalate, and polyvinyl alcohol phthalate.

WO-A-90/04391 (and corresponding GB-A-2223943) discloses that enteric dosage forms of EPA, DHA and other omega-3 polyunsaturated fatty acids overcome the problem of belching and flatulence associated with oral administration of these acids. The exemplified coating is cellulose acetate phthalate/ethyl phthalate but reference is made to the use of polymethacrylate as the coating material.

Belluzzi et al (Dig. Dis. Sci. 39 (1994) 2589–2594) reported a study in which five groups of patients with Crohn's disease were treated with:

Group A—uncoated gelatine capsules containing 500 mg "Purepa" fish oil concentrate (containing EPA 40% and DHA 20%);

Group B—gelatine capsule containing 500 mg "Purepa" fish oil concentrate and coated with a pH 5.5/120 minutes or cellulose acetate trimellate ("CAT") coating;

Group C—gelatine capsule containing 500 mg "Purepa" fish oil concentrate and coated with a pH 5.5/60 minutes CAT coating;

Group D—gelatine capsule containing 500 mg "Purepa" fish oil concentrate and coated with a pH 6.9/120 minutes cellulose acetate phthalate ("CAP") coating; and Group E—uncoated gelatine capsule containing 1000 mg "Max-EPA" triglyceride fish oil (EPA 18% and DHA 10%).

CAP dissolves at pH 6.8 and CAT dissolves at pH 5.5. All the coated capsules disintegrate within 15 minutes at the relevant pH. In the results of the Belluzzi, et al., study, the item before the slash (/) is the pH at which the coating rapidly dissolves the the item following the slash (/) is the time for which the coating is resistant to gastric juice.

The four groups taking Capsule Types A to D took 9 capsules (2.7 g of omega-3 polyunsaturated acid) during meals 3 times daily for 6 weeks and those taking Type E capsules received 12 capsules (3.4 g of omega-3 polyunsaturated acid) daily in divided doses during meals over the 6 week period.

All of the five regimens increased the incorporation of the omega-3 polyunsaturated acid both in plasma and red blood cell phospholipid membranes by displacing arachidonic acid, linoleic acid, and to a lesser extent oleic acid. However, much more of the free omega-3 polyunsaturated fatty acid mixture was absorbed using the capsules containing "Purepa" fish oil concentrate than when using "Max-EPA" triglyceride mixture. The incorporation was coating dependent and it is speculated to be related to the site of capsule-disintegration. The Group C capsules (having the pH 5.5/60 minutes coating) gave the best incorporation of the omega-3 polyunsaturated fatty acids in the plasma and red blood cell phospholipid membranes. The Group D capsules (having the pH 6.9 coating) gave very poor incorporation and 70% of patients in this Group had increased daily bowel motion. Slightly better incorporation was registered with the Group B capsules (having the pH 5.5/120 minutes coating), but 50% of 5 patients in the Group reported diarrhoea.

The Group C capsules used by Belluzzi et al combined both pH and time-dependent release mechanisms and made it possible to avoid capsule-breakdown (pH 5.5) in the stomach-duodenum, and consequently void upper gastrointestinal side-effects. Since they were only gastric resistant for 60 minutes, they allowed quick release of the fish oil concentrate in the small intestine and its complete absorption.

Surprisingly, it has now been found that the optimum combination of absorption and absence of side effects occurs if the release of polyunsaturated fatty acid is controlled to occur in the ileum, especially mid-ileum.

Thus, the present invention provides an oral dosage form, containing as an active principle an omega-3 polyunsaturated acid in free acid form or as a pharmaceutically acceptable salt thereof, which releases the acid in the ileum.

The present invention also provides the use of an omega-3 polyunsaturated acid in free acid form or as a pharmaceutically acceptable salt thereof in the manufacture of a medicament releasing the acid in the ileum for the treatment of inflammatory bowel disease.

Further, the present invention provides the use of said oral dosage forms in the treatment inflammatory bowel disease.

It is preferred that the omega-3 polyunsaturated acid is DHA, EPA or a mixture thereof. It is present in free acid form or as a pharmaceutically acceptable salt thereof and can be present as the sole active principle or with other active principles. Suitably, a fish oil concentrate containing at least 60% by weight DHA and EPA is used.

Omega-3 polyunsaturated acids are readily oxidised and hence an antioxidant usually will be present. The presently preferred antioxidant is gamma-tocopherol but other pharmacologically acceptable antioxidants can be used, for example butylated hydroxy anisole, butylated hydroxy toluene, propyl gallate or a quinone.

The oral dosage form may also contain one or more pharmaceutically acceptable excipients depending upon the precise nature of the dosage form. Suitably, the oral dosage form can be a coated tablet containing the omega-3 polyunsaturated acid in a micro encapsulated form or loaded on a suitable absorbent. However, it is preferred that the oral dosage form is a coated capsule, especially a soft or, more especially, hard gelatine capsule.

The coating must be such as to release the acid in the ileum, preferably in the mid-ileum. Usually, dissolution of the coating will be entirely time dependent but a coating relying on a combination of time and pH dependence can be used. Suitably, the coating is resistant for a period of 30 to 60 minutes at pH 5.5. The presently preferred coating is a neutral polyacrylate such as a poly(ethylacrylate-methylmethacrylate), especially Eudragit NE 30-D (Röhm Pharma GmbH) which has an average molecular weight of about 800,000.

Usually, the omega-3 polyunsaturated acid will be administered in a daily dosage of 20 to 50 mg/kg, especially 30–40 mg/kg. The actual dose will vary depending inter alia on the identity of the omega-3 polyunsaturated acid and the nature and degree of the disorder being treated. Usually, each unit dose will contain 250 to 1000 mg, especially 400 to 800 mg.

The following is a description, by way of example only, of a presently preferred embodiment of the invention.

EXAMPLE 1

Transparent hard gelatine capsules (Elanco Qualicaps size 0; Lilly France SA) were each filled with 500 mg of a fish oil concentrate containing at least 60% by weight DHA and EPA (Incromega 3F60; Croda Universal Ltd, UK). The filled gelatine capsules were film coated with Eudragit® NE 30-D to provide resistance for 30 to 60 minutes at pH 5.5 by spraying with a film coating composition (see below) at 35 ml/min using 0.8 bar pressure at 25° C. and air drying for at least 30 mins at 25° C.

The film coating composition (for 50,000 capsules) was prepared by slowly adding silicon anti-foam emulsion (0.36 mg), brown iron oxide (E 172; 3.00 mg), titanium dioxide (2.35 mg) and talc (10 mg) in succession to water (75 mg) and agitating for 1 to 2 hours to form a very fine dispersion. A 30% aqueous dispersion of a poly(ethylacrylate-methylmethacrylate) having an average molecular weight of about 800,000 (Eudragit® NE 30D; 60 mg) and added to polysorbate 80 (MO 55 F; 0.2 mg) in a little water and the resultant mixture agitated. Silicon anti-foam emulsion (2 or 3 drops) was added to destroy the resultant foam and the aforementioned dispersion was slowly added. The vessel was washed with water (25 mg) and the dispersion stirred for 30 minutes before being filtered (150 μm).

EXAMPLE 2

A double-blind placebo-controlled randomised study was conducted using 78 patients with well established diagnosis of Crohn's disease in clinical remission according to the Crohn's disease activity index (CDAI) and satisfying all the following criteria:

(a) CDAI<150 for at least 3 months but less than 2 years;

(b) at least one abnormal value of alpha-1 acid glycoprotein (>130 mg/d]), erythrocyte sedimentation rate (ESR);

(c) (>40mm/h), or alpha-2 globulin (>0.9 g/dl);

(d) no treatment with 5-aminosalicylate, sulphasalazine or corticosteroids in the previous 3 months, or with immunosuppressive therapy in the previous 6 months;

(e) no previous bowel resection>1 m; and (f) age 18–75 years.

The patients were blindly randomised into two groups of 39 patients to receive daily either 9 enteric-coated hard gelatine capsules containing 500 mg of a fish oil concentrate ("Purepa"; see Table 1) or 9 enteric-coated capsules of identical appearance containing 500 mg of a placebo (Miglyol® 812). The fish oil concentrate contained 40% EPA and 20% DHA. Both sets of capsule were coated with Eudragit NE 30D to resist gastric acid or gut juice for at least 30 min and to disintegrate within 60 min at pH 5.5, allowing release of the fish oil in the small intestine. During the treatment the patients did not take any other medication. The clinical characteristics of both groups of patient are set forth in Table 2.

TABLE 1

COMPOSITION OF CAPSULE CONTENTS

| Lipid profile | Purepa (fish oil) Free fatty acids % | Miglyol (placebo) Neutral oil |
|---|---|---|
| C 14:0 | — | |
| C 16:0 | 0.4 | |
| C 16:1 | 3.2 | |
| C 16:2 | 2.1 | |
| C 16:3 | 2.4 | |
| C 16:4 | 5.2 | |

TABLE 1-continued

COMPOSITION OF CAPSULE CONTENTS

| Lipid profile | Purepa (fish oil) Free fatty acids % | Miglyol (placebo) Neutral oil |
|---|---|---|
| C 18:0 | — | |
| C 18:1 | 0.8 | |
| C 18:2 | 1.5 | |
| C 18:3 | 1.3 | |
| C 18:4 | 6.9 | |
| C 20:1 | — | |
| C 20:3 | 1.5 | |
| C 20:4 (AA) | 1.7 | |
| C 20:5 (EPA) | 42.4 | |
| C 21:5 | 1.6 | |
| C 22:5 | 0.5 | |
| C 22:6 (DHA) | 19.9 | |

TABLE 2

CLINICAL CHARACTERISTICS OF PATIENTS

| | PUREPA | PLACEBO |
|---|---|---|
| MALE | 20 | 19 |
| FEMALE | 19 | 20 |
| AGE (years; median (range)) | 34 (18–67) | 39 (20–65) |
| SMOKERS | 14/39 | 13/39 |
| DURATION OF DISEASE (months, median (range)) | 68 (24–94) | 66 (20–88) |
| PREVIOUS OPERATION <1 m | 14/39 | 13/39 |
| SITE OF INVOLVEMENT | | |
| ileum | 25 | 24 |
| ileum + colon | 14 | 15 |
| CDAI median (range) | 78 (28–120) | 82 (30–112) |
| ESR (mm/h) | 36.9 (SD 27-min 6;max 122) | 35.7 (SD 24-min 12;max 90) |
| ALPHA-2 globulins (g/l) | 9.6 (SD 1.8-min 6.1;max 13.2) | 9.2 (SD 1.3-min 6.5;max 11.9) |
| ALPHA-1 GLYCO-PROTEIN (mg/dl) | 136.8 (SD 52-min 53;max 257) | 137.1 (SD 58-min 60;max 263) |

Each patient in the fish oil group received 1.8 g of EPA and 0.9 g of DHA daily for 12 months. They were examined on entry to the study and at 3, 6 and 12 months or before if symptoms worsened with an increase of CDAI of at least 100 points from baseline value and above 150 for more than 2 weeks. During each visit, laboratory tests were made of blood, kidney, liver, ESR, alpha-1 acid glyco-protein, alpha-2 globulin and CRP (c-AMP-Receptor-Protein). At time 0, 6 months and at the end of the study, 2 ml of packed red cells and polymorphonuclear leucocytes were obtained following the procedure described by Popp-Snijders et al (Scan. J. Clin. Lab. Invest 44 (1984) 39–46) and their membrane lipids were extracted as described by Dodge and Phillips (J. Lipid Res. 8 (1967) 667–675) using a 2:1 mixture of chloroform and methanol containing 0.01% butylated hydroxytoluene (2.6 di-tert-butyl-p-cresol) as antioxidant. Samples were stored under nitrogen at −20° C. for less than 2 weeks prior to separation of the phospholipids and analysis of the omega-3 polyunsaturated fatty acids. Phospholipid fractions were obtained from the extracted lipids using 1-dimensional thin layer chromatography. The samples were spotted in one corner of a silica plate and developed with chloroform/methanol/acetic acid/water (25:14:4:2). The separated phospholipids were transmethylated using 1 N potassium hydroxide in methanol and boron trifluoride in 14% methanol for 10 min at 80° C. Fatty acid methyl esters were then extracted in hexane, resuspended in 100 μl of benzene and analyzed by gas-chromatography equipped with a capillary column (0.32 mm i.d.×25 m), using helium as the carrier gas (flow rate 3ml/min) and flame ionisation detection. The column temperature was programmed between 170° C. and 210° C. at 5°/min with the injector and detector temperatures at 220° C. and 250° C., respectively. Individual fatty acid methyl esters were identified by comparison with commercial standards. Heptadecanoic acid (17:0) was used as the internal standard (1 mg/ml in benzene) and the results expressed as relative percentages.

The difference in the relapse rate in the fish oil and placebo groups was analyzed using the chi-squared test on a 'compliance only' and 'intention to treat' basis. Differences between features of patients in the active and the placebo group were analyzed using the Mann-Whitney U-test, and the laboratory results were analyzed with Student's t-test for paired data (both tests 2-tailed). Kaplan-Maier life-table curves for patients remaining in remission were calculated according to the assigned treatment. Differences in the curves were tested by log rank analysis. Multiple regression analysis was performed between some variables (trial treatment, gender, age, previous surgery, length of disease) and clinical relapses; the forward procedure was used for selecting a more representative model.

In the fish oil group, 1 patient withdrew (moved away) and 4 dropped out because of diarrhoea. In the placebo group, 1 patient withdrew (did not attend the outpatient clinic) and 1 dropped out because of diarrhoea. Diarrhoea started in all 5 cases within the first month of treatment and symptoms did not improve when the daily capsule intake was reduced. This diarrhoea might have been due to the delivery of the capsule contents into the distal part of the gut. The coating is time-dependent (30–60 min at pH 5.5) so if the transit time is short, the capsules would remain intact further along the intestine.

The relapse rate was significantly reduced by the fish oil compared to the placebo group: chi squared 11.75; p=0.0004 (difference 41%, 95% confidence interval (Cl) 16–66). This difference was significant too on an intention to treat analysis: chi squared 9.05; p=0.0026 (difference 32%, 95% (Cl) 12–52).

Table 3 summarises the clinical results and Table 4 summarises the laboratory variables of inflammation at entry and at 12 months in the patients who received the fish oil and were still in remission at the end of the study. No significant decrease in any of the laboratory findings of disease activity occurred in the placebo group. Table 5 shows the incorporation of the main fatty acids into phospholipid membranes (AA=arachidonic acid and LA=linoleic acid). Multiple regression analysis indicated that only the fish oil capsules significantly affected clinical relapse (t=3.16; p=0.002;F ratio=10; p=0.002).

Over a period of 12 months the fish oil capsules used in the study reduced the clinical relapse of Crohn's disease in comparison with placebo by 50%. It is important to note that the patients in the study were in clinical remission for less than 24 months prior to entry, and presented laboratory evidence of inflammation. Patients of this type have about 75% greater risk of relapse in comparison with patients with long previous remission with normal laboratory tests.

The results indicate that the fish oil capsules are the most effective and safe available treatment for preventing clinical relapses in Crohn's disease, with relatively few side effects.

TABLE 3

CLINICAL RESULTS AFTER 12 MONTHS OF TREATMENT

|  | fish oil (n = 39) | placebo (n = 39) |
|---|---|---|
| Withdrew | 1 | 1 |
| REMISSIONS | 23/38 | 10/38 |
| drop-out | 4 | 1 |
| RELAPSES (intention to treat) with drop out | 15/38 (39,5%)* | 28/38 (73,7%) |
|  | *chi square 9.05; p = 0.0026 | |
| excluding drop-outs | 11/34 = 32,4% | 27/37 = 73,0% |
|  | *chi square 11,75; p = 0.0004 | |

TABLE 4

23 PATIENTS GIVEN PUREPA IN REMISSION AFTER 12 MONTHS

|  | TIME 0 | 12 MONTHS |
|---|---|---|
| ESR (mm/h) | 37.8(6–122)SD 25 | 19.5(3–40)SD 11.2 |
|  | p = 0.0002 |  |
| CRP (mg/dl) | 3.6(0.2–9.9)SD 3.4 | 1.0(0.2–3.5)SD 0.9 |
|  | p = 0.001 |  |
| ALFA-2 GLOBULIN (G/DL) | 0.91(0.64–1.32)SD 0.15 | 0.74(0.56–0.91)SD 0.1 |
|  | p = 0.001 |  |
| ALFA-1 GLYCO- PROTEIN (mg/dl) | 137(57–248)SD 49 | 111(69–180)SD 33 |
|  | p = 0.002 |  |
| ALBUMIN (g/dl) | 3.7(3.0–4.4)SD 0.4 | 4.0(3.1–4.7)SD 0.35 |
|  | p = 0.004 |  |
| WBC | 8780(4000–11700)SD 2093 | 7400(3310–11550)SD 2634 |
|  | p = 0.01 |  |

TABLE 5

PERCENTAGE OF MAIN FATTY ACIDS INCORPORATED INTO RBCs

|  | PUREPA | | MIGLYOL | |
|---|---|---|---|---|
|  | TIME 0 | 6 MONTHS | TIME 0 | 6 MONTHS |
| 18:2n-6 LA | 10.2 ± 1 | 7.0 ± 0.8 | 6.4 ± 0.4 | 10.6 ± 1.5 | 9.8 ± 2 | 11.1 ± 1.5 |
| 20:4n-6 AA | 13.9 ± 1.5 | 8.4 ± 1.2 | 7.1 ± 1.2 | 13.5 ± 1.3 | 12.3 ± 1.8 | 14.1 ± 1.2 |
| 20:5n-3 EPA | 0.2 ± 0.1 | 4.1 ± 0.3 | 5.8 ± 0.6 | 0.3 ± 0.1 | 0.1 ± 0.1 | 0.2 ± 0.1 |
| 22:6n-3 DHA | 2.9 ± 0.6 | 7.4 ± 1.2 | 11.4 ± 1.2 | 3.2 ± 0.5 | 2.8 ± 0.7 | 3.0 ± 0.6 |

We claim:

1. An oral dosage form for treating inflammatory bowel disease, containing an active compound selected from the group consisting of omega-3 polyunsaturated acids and pharmaceutically acceptable salts thereof and containing a neutral polyacrylate coating which is resistant to release of the active compound for a period of 30 to 60 minutes at pH 5.5 whereby the active compound is released in the ileum.

2. An oral dosage form comprising a coated capsule containing as an active principle an omega-3 polyunsaturated acid in free acid form or a pharmaceutically acceptable salt thereof, wherein the coating is a neutral polyacrylate whereby the active principle is released in the small intestine.

3. An oral dosage form as claimed in claim 2 wherein the coating is resistant to release of the omega-3 polyunsaturated acid for a period of 30 to 60 minutes at pH 5.5.

4. An oral dosage form as claimed in claim 2 wherein the coating is a poly(ethylacrylate-methylmethacrylate).

5. An oral dosage form as claimed in claim 4 wherein the coating comprises iron oxide, titanium dioxide, and talc.

6. An oral dosage form as claimed in claim 5 wherein the coating contains by ratio about 3 mg iron oxide, about 2.35 mg titanium dioxide, and about 10 mg talc to about 60 mg of poly(ethylacrylate-methylmethacrylate).

7. An oral dosage from as claimed in claim 2 wherein said acid is eicosapenta-5,8,11,14,17-enoic acid, docosahexa--4,7,10,13,16,19-enoic acid or a mixture thereof.

8. An oral dosage form as claimed in claim 7 wherein the eicosapenta-5,8,11,14,17-enoic acid, docosahexa-4,7,10,13,16,19-enoic acid or mixture thereof is present in an oil constituent in a percentage of at least 60% w/w.

9. An oral dosage form as claimed in claim 2 wherein said acid is present as the sole active principle.

10. An oral dosage form as claimed in claim 2 wherein said active principle is an omega-3 polyunsaturated acid in free acid form or a pharmaceutically acceptable salt thereof except for a lithium salt thereof.

11. An oral dosage form as claimed in claim 2 wherein the capsule is a hard or soft gelatin capsule.

12. An oral dosage form as claimed in claim 2 containing as an active principle a unit dose of 250 to 1,000 mg.

13. A method of treating inflammatory bowel disease or reducing clinical relapse thereof, which comprises administering to a patient an effective amount of an oral dosage form as claimed in claim 2.

14. A method as claimed in claim 13 wherein the inflammatory bowel disease is Crohn's disease.

15. A method as claimed in claim 14 wherein patients are in clinical remission for less than 24 months prior to treatment.

16. A method as claimed in claim 13 which comprises administering a daily dosage of 20 to 50 mg/kg omega-3 polyunsaturated acid.

17. An oral dosage form comprising a capsule containing eicosapenta-5,8,11,14,17-enoic acid, docosahexa-4,7,10,13,16,19-enoic acid or a mixture thereof, and coated with poly(ethylacrylate-methylmethacrylate).

* * * * *

(12) EX PARTE REEXAMINATION CERTIFICATE (10037th)
United States Patent
Buser et al.

(10) Number: US 5,792,795 C1
(45) Certificate Issued: Feb. 12, 2014

(54) TREATMENT OF INFLAMMATORY BOWEL DISEASE USING ORAL DOSAGE FORMS OF OMEGA-3 POLYUNSATURATED ACIDS

(75) Inventors: Thomas Buser, Ziefen (CH); Emilio P. Camporesi, Ziefen (CH)

(73) Assignee: Chrysalis Pharma AG, Sachsein (CH)

Reexamination Request:
No. 90/012,827, Apr. 3, 2013

Reexamination Certificate for:
Patent No.: 5,792,795
Issued: Aug. 11, 1998
Appl. No.: 08/687,329
Filed: Aug. 7, 1996

(21) Appl. No.: 90/012,827

(22) PCT Filed: May 13, 1996

(86) PCT No.: PCT/EP96/02038
§ 371 (c)(1),
(2), (4) Date: Aug. 7, 1996

(87) PCT Pub. No.: WO96/36329
PCT Pub. Date: Nov. 21, 1996

(30) Foreign Application Priority Data

May 15, 1995 (GB) ...................................... 9509764

(51) Int. Cl.
*A61K 9/48* (2006.01)
*A61K 31/202* (2006.01)
*A61K 31/185* (2006.01)

(52) U.S. Cl.
CPC ............. *A61K 9/4891* (2013.01); *A61K 31/202* (2013.01); *Y10S 514/963* (2013.01)
USPC .......................................... 514/560; 514/963

(58) Field of Classification Search
None
See application file for complete search history.

(56) References Cited

To view the complete listing of prior art documents cited during the proceeding for Reexamination Control Number 90/012,827, please refer to the USPTO's public Patent Application Information Retrieval (PAIR) system under the Display References tab.

*Primary Examiner* — Evelyn Huang

(57) ABSTRACT

Inflammatory bowel disease, especially Crohn's disease and ulcerative colitis, is treated by administration of an oral dosage form, containing as an active principle an omega-3 polyunsaturated acid in free acid form or as a pharmaceutically acceptable salt thereof, which releases the acid in the ileum. Preferably the oral dosage form is a gelatine capsule coated with a poly(ethylacrylate-methylmethacrylate).

EX PARTE REEXAMINATION CERTIFICATE ISSUED UNDER 35 U.S.C. 307

THE PATENT IS HEREBY AMENDED AS INDICATED BELOW.

Matter enclosed in heavy brackets [ ] appeared in the patent, but has been deleted and is no longer a part of the patent; matter printed in italics indicates additions made to the patent.

ONLY THOSE PARAGRAPHS OF THE SPECIFICATION AFFECTED BY AMENDMENT ARE PRINTED HEREIN.

Column 3, lines 3-10:
The Group C capsules used by Belluzzi et al combined both pH and time-dependent release mechanisms and made it possible to avoid capsule-breakdown (pH 5.5) in the stomach-duodenum, and consequently [void] *avoid* upper gastrointestinal side-effects. Since they were only gastric resistant for 60 minutes, they allowed quick release of the fish oil concentrate in the small intestine and its complete absorption.

AS A RESULT OF REEXAMINATION, IT HAS BEEN DETERMINED THAT:

Claims 10 and 13-17 are cancelled.

Claims 1-9, 11 and 12 are determined to be patentable as amended.

New claims 18-33 are added and determined to be patentable.

1. An oral dosage form for treating inflammatory bowel disease, [containing] *comprising:*
   *a coated gelatin capsule;*
   an active compound selected from the group consisting of omega-3 polyunsaturated acids [and pharmaceutically acceptable salts thereof] *in free acid form,* and [containing,] a neutral polyacrylate coating *on said gelatin capsule* which is resistant to release of the active compound for a period of 30 to 60 minutes at pH 5.5 whereby the active compound is released in the ileum;
   *wherein said coating is applied as an aqueous coating dispersion directly on said gelatin capsule.*

2. An oral dosage form comprising a coated *gelatin* capsule, containing:
   *as an active principle,* an omega-3 polyunsaturated acid *in free acid form* [or a pharmaceutically acceptable salt thereof];
   wherein the coating is a neutral polyacrylate whereby the active principle is released in the small intestine;
   *wherein said coating is applied as an aqueous coating dispersion directly on said gelatin capsule.*

3. [An] *The* oral dosage form as claimed in claim 2, wherein the coating is resistant to release of the omega-3 polyunsaturated acid for a period of 30 to 60 minutes at pH 5.5.

4. [An] *The* oral dosage form as claimed in claim 2, wherein the coating is a poly(ethylacrylate-methylmethacrylate).

5. [An] *The* oral dosage form as claimed in claim 4, wherein the coating comprises iron oxide, titanium dioxide, and talc.

6. [An] *The* oral dosage form as claimed in claim 5, wherein the coating contains by ratio about 3 mg iron oxide, about 2.35 mg titanium dioxide, and about 10 mg talc to about 60 mg of poly(ethylacrylate-methylmethacrylate).

7. [An] *The* oral dosage from as claimed in claim 2, wherein said acid is eicosapenta-5,8,11,14,17-enoic acid, docosahexa--4,7,10,13,16,19-enoic acid or a mixture thereof.

8. [An] *The* oral dosage form as claimed in claim 7, wherein the eicosapenta-5,8,11,14,17-enoic acid, docosahexa-4,7,10,13,16,19-enoic acid or mixture thereof is present in an oil constituent in a percentage of at least 60% w/w.

9. [An] *The* oral dosage form as claimed in claim 2, wherein said acid is present as the sole active principle.

11. [An] *The* oral dosage form as claimed in claim 2, wherein the capsule is a hard or soft gelatin capsule.

12. [An] *The* oral dosage form as claimed in claim 2, containing [as an active principle] a unit dose of 250 to 1,000 mg *of active principle.*

*18. An oral dosage form, comprising:*
   *a coated gelatin capsule;*
   *an active compound selected from the group consisting of omega-3 polyunsaturated acids in free acid form, and*
   *a neutral polyacrylate coating on said gelatin capsule;*
   *wherein said coating is resistant to release of the active compound for a period of 30 to 60 minutes at pH 5.5 whereby the active compound is released in the small intestine;*
   *wherein said coating is applied as an aqueous coating dispersion directly on said gelatin capsule.*

*19. An oral dosage form, comprising:*
   *a gelatin capsule containing, as an active compound, eicosapenta-5,8,11,14,17-enoic acid, docosahexa-4,7,10,13,16,19-enoic acid or a mixture thereof, each in free acid form; and*
   *a neutral poly(ethylacrylate-methylmethacrylate) coating on said gelatin capsule;*
   *wherein said coating is resistant to release of the active compound for a period of 30 to 60 minutes at pH 5.5 whereby the active compound is released in the small intestine;*
   *wherein said coating is applied as an aqueous coating dispersion directly on said gelatin capsule.*

*20. The oral dosage form as claimed in claim 18, wherein the coating is a poly(ethylacrylate-methylmethacrylate).*

*21. The oral dosage form as claimed in claim 18, wherein the coating comprises iron oxide, titanium dioxide, and talc.*

*22. The oral dosage form as claimed in claim 18, wherein the coating contains by ratio about 3 mg iron oxide, about 2.35 mg titanium dioxide, and about 10 mg talc to about 60 mg of poly(ethylacrylate-methylmethacrylate).*

*23. The oral dosage from as claimed in claim 18, wherein said acid is eicosapenta-5,8,11,14,17-enoic acid, docosahexa--4,7,10,13,16,19-enoic acid or a mixture thereof.*

*24. The oral dosage form as claimed in claim 18, wherein the eicosapenta-5,8,11,14,17-enoic acid, docosahexa-4,7,10,13,16,19-enoic acid or mixture thereof is present in an oil constituent in a percentage of at least 60% w/w.*

*25. The oral dosage form as claimed in claim 18, wherein said acid is present as the sole active principle.*

*26. The oral dosage form as claimed in claim 18, wherein the capsule is a hard or soft gelatin capsule.*

*27. The oral dosage form as claimed in claim 18, containing a unit dose of 250 to 1,000 mg of active principle.*

*28. The oral dosage form as claimed in claim 19, wherein the coating comprises iron oxide, titanium dioxide, and talc.*

*29. The oral dosage form as claimed in claim 19, wherein the coating contains by ratio about 3 mg iron oxide, about*

2.35 mg titanium dioxide, and about 10 mg talc to about 60 mg of poly(ethylacrylate-methylmethacrylate).

30. The oral dosage form as claimed in claim 19, wherein the eicosapenta-5,8,11,14,17-enoic acid, docosahexa-4,7,10,13,16,19-enoic acid or mixture thereof is present in an oil constituent in a percentage of at least 60% w/w.

31. The oral dosage form as claimed in claim 19, wherein said acid is present as the sole active principle.

32. The oral dosage form as claimed in claim 19, wherein the capsule is a hard or soft gelatin capsule.

33. The oral dosage form as claimed in claim 19, containing a unit dose of 250 to 1,000 mg of active principle.

* * * * *